US005747435A

United States Patent [19]
Patel

[11] Patent Number: 5,747,435
[45] Date of Patent: May 5, 1998

[54] MILD FOAMING AND CONDITIONING DETERGENTS

[75] Inventor: Amrit M. Patel, Dayton, N.J.

[73] Assignee: Colgate-Palmolive Company, New York, N.Y.

[21] Appl. No.: 682,494

[22] Filed: Jul. 17, 1996

Related U.S. Application Data

[60] Provisional application No. 60/001,700, Aug. 1, 1995.
[51] Int. Cl.$^6$ .............................. C11D 1/12; C11D 1/88; C11D 1/94; C11D 9/36
[52] U.S. Cl. .................. 510/119; 510/124; 510/125; 510/127; 510/131; 510/405; 510/409; 510/410; 510/411; 510/414; 510/416; 510/422; 510/426; 510/428; 510/429; 510/499; 510/503; 510/504
[58] Field of Search ................... 510/119, 124, 510/125, 127, 131, 405, 409, 410, 411, 414, 416, 422, 426, 428, 429, 499, 503, 504

[56] References Cited

U.S. PATENT DOCUMENTS

| | | | |
|---|---|---|---|
| 5,641,480 | 6/1997 | Vermeer | 424/70.24 |
| 5,648,323 | 7/1997 | Coffindaffer et al. | 510/122 |

FOREIGN PATENT DOCUMENTS

| | | |
|---|---|---|
| 254653 | 1/1988 | European Pat. Off. . |
| 524434 | 1/1994 | European Pat. Off. . |
| 4324358 | 7/1993 | Germany . |
| WO 94/06410 | 3/1994 | WIPO . |
| WO 94/14947 | 7/1994 | WIPO . |
| WO 96/29983 | 10/1996 | WIPO . |

*Primary Examiner*—Christine Skane
*Assistant Examiner*—Charles Boyer
*Attorney, Agent, or Firm*—Richard J. Ancel; Rosemary M. Miano

[57] ABSTRACT

Composition useful as 2-in-1 cleansing products are disclosed that are extremely mild to skin and hair, which use neutralized, essentially chargeless, ionic complexes of fatty amines and fatty acids to deliver various levels of conditioning; neutralized, essentially chargeless, ionic complexes of a detersive surfactant comprising a water soluble cationic surfactant and/or polymer complexed with one or more anionic surfactants; or an amphoteric surfactant complexed with one or more anionic surfactants; or a water soluble cationic surfactant and/or polymer complexed with one or more amphoteric surfactants; or a water soluble cationic surfactant and/or polymer complexed with one or more anionic surfactants and an amphoteric surfactant; detersive surfactant-soluble but water-insoluble silicones or derivatives thereof; and water. These products exhibit true 2-in-conditioning properties, and are lower in cost than current 2 in 1 products. Clear or opacified products can be formulated.

33 Claims, No Drawings

MILD FOAMING AND CONDITIONING DETERGENTS

This application is based on Provisional Application Number 60/001,700 filed Aug. 1, 1995.

FIELD OF THE INVENTION

The instant invention is generally directed to novel, ultra mild "2-in-1" conditioning aqueous detergent products, including shampoos, antidandruff shampoos, and a variety of body care products, such as shower gels, liquid soaps-with and without antibacterial agents, facial cleansers, baby washes, baby shampoos and the like, having detersive surfactant systems based upon use of balanced molar proportions of the essential anionic detergent, anionic hydrotropic sulfonate or sulfate, amphoteric detergent and cationic conditioner ingredients. The desired balance is achieved by having the sum (on a molar basis) of the anionic detergent and hydrotropic sulfonate/sulfate substantially equal to the sum (on a molar basis) of the amphoteric detergent and any cationic conditioner ingredient. The resultant novel aqueous detergent products deliver excellent cleansing and foaming properties without irritation to skin and hair; provide true 2-in-1 conditioning properties to the hair and skin; and are lower in cost than current "2-in-1" products. A further benefit is that these detergents are in solution form and are crystal clear, although, if desired, they can be opacified.

BACKGROUND OF THE INVENTION

Currently, commercially available, "2-in-1", or conditioning shampoos, are optically opaque. This is due to the fact that the conditioning agents incorporated therein are essentially water insoluble. For example, when high-molecular weight silicone derivatives are added to achieve the conditioning benefits, it has been found that it is difficult to formulate silicone-containing shampoos that are stable and do not suffer from the separating out of the silicone ingredient. The most accepted way to incorporate these silicone conditioning agents in such conditioning shampoos is to disperse, suspend, or emulsify them, which results in the opacification of these products and sometimes results in unstable products due to the separation of the emulsified or suspended silicone.

While the above-described "2-in-1" conditioning shampoos have achieved a great deal of success in the marketplace, such products suffer, at least among a certain segment of consumers, negative attributes of poor appearance, decreased foam, reduced viscosity, and physical instability because the conditioning materials therein are not completely dissolved. The patent literature relating to detergent compositions which include water-insoluble, hair and skin conditioning materials reflects a variety of approaches designed to overcome the above mentioned disadvantages. More specifically, the patent literature teaches a variety of agents that disperse, suspend, or emulsify such conditioning agents. For example, U.S. Pat. No. 4,741,855 to Grote et al teaches the use of long chain ($C_{16}$–$C_{22}$) acyl derivatives, such as ethylene glycol distearate or long chain ($C_{16}$–$C_{22}$) amine oxides, as suspending agents. U.S. Pat. No. 5,152,914 to Forster et al teaches the use of suspending agents chosen from polyethylene glycol mono- or diesters of $C_{16}$–$C_{22}$ fatty acids having from 2 to 7 ethylene oxide groups. Also, U.S. Pat. No. 4,997,641; U.S. Pat. No. 5,106,613; U.S. Pat. No. 5,213,716; U.S. Pat. No. 5,346,642; and U.S. Pat. No. 5,348,736, all assigned to the assignee of the instant invention, disclose the use of chain ($C_{24}$–$C_{45}$) alcohols and ethoxylated alcohols as suspending agents. Alternatively, U.S. Pat. No. 4,559,227 to Chandra et al discloses conditioning shampoos in the form of clear solutions wherein blends of amine-functional siloxane polymers and nonionic surfactants of the alkanolamide or amine oxide type are dissolved in aqueous solutions containing typical anionic and amphoteric detergents used in shampoos. However, the commercial availability of the latter compositions has not been assessed.

Now it has been found that it is possible to formulate aqueous detergent compositions containing balanced molar proportions of anionic, amphoteric and cationic ingredients that are crystal clear (although they can be opacified if desired) which exhibit true "2-in-1" conditioning properties. Furthermore, the resultant compositions are ultra mild and thus do not cause irritation to skin or hair. Additionally, these compositions are high foaming, and can be manufactured in a more cost-effective and less energy intensive manner than the commercially available silicone-containing conditioning shampoos, which are in emulsion, suspension or dispersion form.

It is recognized that the prior art discloses compositions containing essentially equimolar quantities of anionic surfactant and amphoteric surfactant. For example, U.S. Pat. No. 3,950,417 of Verdicchio et al. discloses a shampoo containing nonionic surfactant, a surfactant betaine and an anionic surfactant wherein the molar ratio of betaine to anionic is from 0.9:1 to 1.1:1. However, the nonionic detergent is the principal surfactant in the preferred compositions which of necessity exhibit reduced foaming. Similarly, U.S. Pat. No. 4,246,131 of Lohr discloses a low irritant, clear composition containing an equimolar mixture of surfactant betaine and alkonalomine neutralized, anionic, alkyl sulfate detergent. However, the prior art compositions do not include water-insoluble conditioning agents or anionic hydrotropic sulfonates/sulfates and do not recognize the need for balanced molecular proportions of the anionic, amphoteric and cationic ingredients therein. Therefore, said compositions should not provide effective hair and skin conditioning benefits.

On the other hand, European Application EP 0 294 894 A2 discloses an ion pair complex of an anionic surfactant, an alkyl amine and a wax as a conditioning agent and discloses anionic surfactant based shampoos containing said complex as a conditioning agent. However, again there is no recognition of the need for balanced molar proportions of anionic, amphoteric and cationic ingredients in the final composition. Thus, the need still exists for a clear, ultra mild, foaming, conditioning composition.

SUMMARY OF THE INVENTION

As described above, the present invention primarily resides in the discovery that foaming and conditioning compositions which are mild can be prepared in the form or clear liquids if balanced molecular proportions of selected anionic detergents, anionic sulfonate/sulfate hydrotropes, amphoteric surfactants and water-insoluble cationic, hair and skin conditioning agents are employed.

Broadly, the present invention relates to a clear, ultra mild, aqueous, foaming and conditioning detergent composition comprising, by weight:

A. about 5% to about 40% of a detersive surfactant mixture of:

(1) about 2% to about 14% of an anionic detergent selected from the group consisting of $C_8$–$C_{18}$ alkyl sulfates, $C_8$–$C_{18}$ alkyl ethenoxy ether sulfates containing 1 to 5 ethenoxy groups in the molecule, $C_{10}$–$C_{18}$ acyl isethionates, $C_{10}$–$C_{20}$ alkyl sulfonates, $C_{10}$–$C_{22}$ alkylene sulfonates, and mixtures thereof;

(2) about 0.5% to about 5% of an anionic hydrotropic, $C_1$–$C_3$ alkyl benzene sulfonate or $C_5$–$C_6$ alkyl sulfate; and (3) about 2.5% to about 21% of an amphoteric surfactant selected from the group consisting of $C_8$–$C_{18}$ alkyl betaines, and sulfobetaines, $C_8$–$C_{18}$ alkylamido, $C_2$–$C_3$ alkyl betaines and sufobetaines, $C_8$–$C_{18}$ alkyl amphoacetates, $C_8$–$C_{18}$ alkyl amphopropionates, and mixtures thereof;

B. about 0.05% to about 9% of a water-insoluble conditioning agent which is soluble in said aqueous detersive surfactant mixture selected from the group consisting of:

(1) about 0.05% to about 5% of a complex of essentially equimolar amounts of a $C_8$–$C_{18}$ (EtO)$_{1-10}$ fatty acid, and a $C_8$–$C_{18}$ alkyl (EtO)$_{0-10}$ dimethyl amine;

(2) about 0.25% to about 3% of a water-insoluble silicone soluble in said aqueous detersive surfactant mixture selected from the group consisting of polydimethylsiloxane polyether copolymers, polydimethylsiloxanes containing an amino substituent, polydimethylsiloxanes containing at least one quaternary ammonium substituent and mixtures thereof; and (3) a mixture of B(1) and/or B(2) with about 0.05% to about 1.0% of a polyquaternary compound selected from the group consisting of a quaternized cellulosic polymer and a mixture of said quaternized cellulosic polymer with a non-cellulosic quaternary conditioning polymer; and C. the balance of an aqueous medium; the sum of the moles of anionic detergent and anionic hydrotropic sulfonate/sulfate being substantially equal to the sum of the moles of amphoteric detergent and cationic conditioning agent at a pH in the range of 5.5 to 7.0 and said composition being effective to deliver said conditioning agent in water-insoluble form at use concentrations of the composition in water.

In a preferred aspect, the described invention contains as the conditioning agent a mixture of (a) a quaternized cellulose polymer, (b) a complex of essentially equimolar amounts of $C_8$–$C_{18}$ (EtO)$_{1-10}$ carboxylic acid and $C_8$–$C_{18}$ alkyl (EtO)$_{0-10}$ dimethyl amine and (c) polydimethylsiloxane polyoxy ($C_2$–$C_3$) alkylene copolymer and, in addition, 0.05% to 1.0% of a mono $C_{12}$–$C_{18}$ alkyl or di-$C_{12}$–$C_8$ alkyl (EtO)$_{3-20}$ quaternary ammonium compound. The preferred compositions exhibit enhanced conditioning properties due to the use of the mixture of conditioning agents and also exhibit enhanced anti-static properties due to the inclusion of the mono-alkyl or di-alkyl (EtO) 3–20 quaternary compound.

In one further preferred aspect, the inventive compositions enable a manufacturer to market a line of conditioning shampoo products having variable conditioning properties. More specifically, by utilizing the specified conditioning materials individually and in mixtures, a line of conditioning shampoos providing low, medium and high conditioning effects can be provided.

DETAILED DESCRIPTION OF THE INVENTION

Anionic Detergents

The suitable anionic detergents are employed in the form of their water-soluble salts and the salt forming cation usually is selected from the group consisting of sodium, potassium, ammonium and mono-, di- and tri- $C_2$–$C_3$ alkanolammonium, with the sodium and ammonium cations being preferred.

The suitable anionic detergents include the following:

1. The $C_8$–$C_{18}$ alkyl ether ethenoxy sulfates of the formula

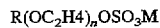

$$R(OC_2H_4)_nOSO_3M$$

wherein n is 1 to 5. These sulfates differ from the primary alkyl sulfate detergent in the number of moles of ethylene oxide (1–5) reacted with one mole of alkanol in forming the ethoxylated alkanol which is sulfated and neutralized to form this anionic detergent. Preferred alkyl ether ethenoxy sulfates contain 12 to 16 carbon atoms in the alkyl group and contain two to three ethylene oxide groups per mole of alkanol.

2. The $C_8$–$C_{18}$ alkyl sulfates which are usually obtained by sulfating $C_8$–$C_{18}$ alkanols obtained by reducing the glycerides of tallow or coconut oil. Preferred alkyl sulfates contain 10 to 16 carbons in the alkyl group.

3. The O-$C_8$–$C_{18}$ acyl isethionates may be produced by neutralizing the reaction product of a $C_8$–$C_{18}$ alkanoic acid with 2-hydroxyethanesulfonic acid. Similar to the sarcosines and taurines, the preferred isethionates contain 12 to 14 carbon atoms in an acyl group obtained by reduction of coconut oil.

4. The $C_{10}$–$C_{20}$ paraffin sulfonates obtained, for example, by reacting an alpha-olefin with bisulfite. Preferred alkane sulfonates contain 13 to 17 carbon atoms in the alkyl group.

5. The $C_{10}$–$C_{22}$ olefin sulfonates which may be obtained by sulfating the appropriate olefin. Preferred olefin sulfonates contain from 14 to 16 carbon atoms in the alkyl group and are obtained by sulfonating an alpha-olefin.

While mixtures of the foregoing anionic detergents may be employed, the preferred anionic detergents are the alkyl ethenoxy ether sulfates and the alkyl sulfates.

The proportion of the anionic detergent in the claimed compositions generally will be in the range of about 2% to about 14% by weight, preferably in the range of 4% to 11% by weight and most preferably in the range of 6% to 8% by weight.

Other Anionic Surfactant

In addition to the anionic detergent discussed above, the described inventive compositions include anionic, hydrotropic $C_1$–$C_3$ alkyl substituted benzene sulfonates and $C_5$–$C_6$ alkyl sulfates. These materials are classified as surfactant-hydrotropes and serve to solubilize the anionic and amphoteric detergent in the aqueous medium. Also, it is believed that these materials assist in removing soil from the substrates being cleaned. Usually, these materials are used in the form of their water soluble sodium, potassium and ammonium salts. Suitable hydrotropic sulfonate and sulfate salts include the salts of toluene sulfonate, xylene sulfonate, cumene sulfonate, $C_5$–$C_6$ alkyl sulfate and mixtures thereof.

The proportion of the hydrotropic sulfonate or sulfate material generally will be in the range of about 0.5% to about 5% by weight of the resultant composition. Preferably the range of this material will be about 0.5% or 1% to 4% by weight of the final composition.

Amphoteric Surfactants

Generally, the amphoteric surfactant components will be selected from the group consisting of $C_8$–$C_{18}$ alkyl betaines and sulfobetaines, and $C_8-C_{18}$ alkyl amphoacetates and propionates. The suitable betaines and sulfobetaines have the following formula:

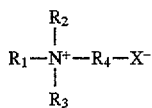

wherein $R_1$ is an alkyl group having 8 to about 18 carbon atoms, preferably 10 to 16 carbon atoms or the amido radical:

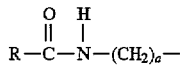

wherein RCO is an acyl group having 8 to about 18 carbon atoms and a is the integer 1 to 4: $R_2$ and $R_3$ are each alkyl groups having 1 to 3 carbon atoms and preferably 1 carbon; $R_4$ is an alkylene or hydroxyalkylene group having from 1 to 4 carbon atoms and optionally, one hydroxyl group; and X is an anion selected from the group consisting of $SO_3=$ and $COO=$. Typical betaines and amido alkyl betaines include decyl dimethyl betaine or 2-(N-decyl-N,N-dimethylammonio) acetate, cocodimethyl betaine or 2-(N-coco-N,N-dimethylammonio) acetate, myristyl dimethyl betaine, palmityl dimethyl betaine, lauryl dimethyl betaine, cetyl dimethyl betaine, stearyl dimethyl betaine, cocoamidopropyl dimethyl betaine and laurylmidoethyl dimethyl betaine. Typical sulfobetaines or sultaines similarly include cocodimethyl sulfobetaine, or 3-(N-coco-N,N-dimethylammonio) propane-1 sulfonate, myristyl dimethyl sulfobetaine, lauryl dimethyl sulfobetaine, cocoamidoethyl-sulfobetaine and cocamidopropylhydroxy sultaine.

Other suitable amphoteric detergents are the $C_8-C_{18}$ alkyl amphoacetates and propionates corresponding to the following formula:

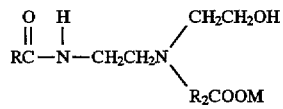

wherein RC(O) is a $C_8-C_{18}$ acyl group, $R_2$ is a $C_1-C_2$ alkyl group and M is a salt forming group such as sodium or potassium. A substitute for the described amphoacetate or amphopropionate compound is sodium cocoamphohydroxypropyl sulfonate. Sodium cocoamphoaetate is a preferred material.

The proportion of the amphoteric detergent generally will be in the range of about 2.5% to about 21% by weight of the final composition. Preferably the proportion of amphoteric surfactant will be selected from the range of about 4% to about 13% by weight and most preferably from the range of about 6% to about 10% by weight of the final composition.

In the preferred compositions, the proportion of the detergent mixture will be from about 8% to 28% by weight of the composition; and in the most preferred compositions the proportion of said detergent mixture will be from 13% to 22% by weight.

Conditioning Agents

The essential water-insoluble conditioning agent which is employed in the inventive compositions is soluble in the above-described aqueous detersive surfactant mixture and generally will be selected from the group consisting of (1) essentially equimolar complexes of $C_8-C_{18}$ alkyl ethoxy carboxylic acids and $C_8-C_{18}$ alkyl ethoxy dimethyl amines; (2) silicones soluble in the aqueous detergent mixture herein selected from the group consisting of polydimethylsiloxane polyether copolymers, polydimethylsiloxanes containing an amino substitutuent and mixtures thereof; and (3) a mixture of (1) and(or (2) with a quaternized cellulosic polymer or a mixtures of quaternized cellulosic polymer with minor proportions of non-cellulosic quaternary conditioning polymers.

The equimolar complexes of $C_8-C_{18}$ alkyl ethoxy carboxylic acids and $C_8-C_{18}$ alkyl ethoxy dimethyl amines are believed to form amine salts which provide conditioning properties in the described compositions. Usually, the ethoxylated carboxylic acid will contain from 1 to 10 ethoxy groups and preferably from 2 to 6 ethoxy groups. On the other hand, the higher alkyl dimethyl amine may contain from 0 to 10 ethoxy groups. While the amine salts are believed to form when equimolar amounts of said carboxylic acid and said dimethyl amine are present, the presence of excess dimethylamine on a molar basis does not have an adverse effect on the conditioning properties of the amine salt and a slight molar excess of said amine may be preferred. Preferred carboxylic acids are the $C_{10}-C_{14}$ $(EtO)_{2-6}$ carboxylic acids and preferred amines are the $C_{14}-C_{18}$ alkyl and $C_{14}-C_{18}$ alkyl amido propyl dimethyl amines.

Generally the proportion of the amine salt formed by the complex of $C_8-C_{18}$ alkyl ethoxy carboxylic acid and the $C_8-C_{18}$ alkyl dimethyl amine will be about 0.05% to 5%, preferably 0.1% to 2.5%, and most preferably about 0.15% to 1.5%, by weight of the resultant composition. When this complex is used as sole conditioner, a low level of conditioning is perceived by the user.

Surfactant-Soluble, Water-Insoluble Silicones or Silicone-Derivatives

The silicones or silicone-derivatives that are useful in the present invention are those that are soluble in and compatible with the above described aqueous detersive surfactant mixture, but are insoluble in water. This allows them to be formulated into detergent compositions that are initially transparent, but which, if desired, can be opacified or pearlized by adding recognized pearlizing/opacifying ingredients such as ethylene glycol distearate or polystyrene. Suitable silicones include trimethylsilylamodimethicone purchased under the trade name Dow Corning Q2-8220—an amine functional polydimethylsiloxane; copolymers of polydimethylsiloxane and a poly $C_2-C_3$ alkylene ether purchased under the tradenames Dow Corning 190, Dow Corning 2-5324 and Dow Corning Q2-5220; and polydimethyl siloxanes having at least one quaternary ammonium moiety, preferably two quaternary ammonium moieties. The latter silicone is available commercially under the tradename ABIL-QUAT 3270 for example. If silicones other than those above are employed, the resultant compositions usually are not clear because part of the polydimethylsiloxane is present in water insoluble form.

The proportion of the surfactant soluble, water insoluble silicone in the inventive composition broadly will be in the range of about 0.25% to about 3%, preferably 0.5% to 2%, most preferably 0.7% to 1.5%, by weight. When said silicone is the sole conditioning agent present, a composition having a low conditioning effect is achieved—a conditioning value of 2.5 for example. However, when a mixture of the described amine salt, cellulose polyquat and the described silicone is employed as the conditioning agent, the resultant composition exhibits high conditioning properties—a value of 7.0 or more in the applicable test.

Cationic Polymers

The water-insoluble conditioning complex of carboxylic acid and amine and the water insoluble silicone conditioning agents are soluble in the described aqueous detergent mixture, but are rendered water-insoluble when the resultant detergent compositions are diluted with water during use. In addition, either one or both of these conditioning agents may be further employed in admixture with a cationic cellulosic polymer. Because the cationic cellulosic polymers are water soluble and soluble in the aqueous detergent mixture, clear detergent mixtures can be prepared when the cationic cellulosic polymers are employed as the sole conditioning agent.

The suitable hair conditioning, cationic polymers are derivatives of natural polymers such as cellulose and gums. These derivatives generally are water-soluble to the extent of at least 0.5% by weight at 20° C. Generally, such polymers have more than 10 monomer units in their molecules and a molecular weight of about 1000 to about 1,000,000, preferably 2000 to 500,000. Usually, the lower the molecular weight, the higher the degree of substitution by the cationic, usually quaternary, group.

Suitable natural polymers which may be converted into the desired cationic polymers are hydroxy alkyl celluloses and alkyl hydroxy alkyl celluloses. Cationic hydroxy alkyl celluloses and their preparation are described in B.P. No. 1,166,062 assigned to Union Carbide. These hydroxy ethyl celluloses are marketed under the trade designation JR 125, JR 30M and JR 400 and are believed to have a molecular weight of 150,00 to 400,000 and a degree of substitution of a quaternary group of about 0.3. Alkyl hydroxy alkyl celluloses having the same formula as hydroxy alkyl cellulose, but with additional alkyl substituents at other sites on the anhydroglucose unit also are available. More particularly, the ethyl hydroxy ethyl celluloses are available under the tradename "Modocoll" with a molecular weight in the range of about 50,000 to 500,000 and a degree of substitution of about 0.1 to 0.8.

Other suitable natural cationic polymers are the galactomannan gums, e.g., guar gum and hydroxy alkylated guar gum. The molecular weight of guar gum is believed to be from about 100,000 to 1,000,000. A suitable cationic guar gum carrying the group —CH$_2$CH=CH CH$_2$N (CH$_3$)$_3$C— with a degree of substitution of about 0.2 to 0.8 is commercially available under the tradenames Jaguar C-17 and C-13. The preferred cationic cellulose polymer is Polyquaternium 10 which is a polymeric quaternary ammonium salt of hydroxyethyl cellulose reacted with a trimethyl ammonium substituted epoxide.

The proportion of the cationic natural polymer usually will be from about 0.05% to about 1%, preferably 0.1% to 0.8%, most preferably from 0.2% to 0.7%, by weight of the final composition. The cationic polymer provides for enhanced style control and conditioning. When Polyquaternium 10 is employed as the sole conditioning agent, a product with moderate conditioning results.

When the cationic natural cellulose or galactomannan gum polymers are present in the inventive compositions, up to about one half the weight of said natural polymer may be substituted by a second non-cellulosic, cationic polymer, having conditioning properties provided that the non-cellulosic cationic polymer is soluble in the final composition. Exemplary of such cationic polymers are dialkyldiallyl ammonium salt (e.g., halide) homopolymers or copolymers, e.g., dimethyidiallyl ammonium chloride homopolymer, dimethyldiallyl ammonium chloride/acrylamide copolymer containing at least 60% dimethyldiallyl ammonium chloride monomer, dimethyidiallyl ammonium chloride/acrylic acid copolymer containing at least 90% dimethyldiallyl ammonium chloride monomer, vinyl imidazolelvinyl pyrrolidone copolymers containing at least 50% vinyl imidazole and polyethyleneimine. Currently, the preferred cationic polymers are Merquat 100 [a polymer of diallyldimethyl ammonium chloride (charge density of 126)] and Luviquat 905 [a 95% vinyl imidazole/5% vinylpyrrolidone copolymer (charge density of 116)]. Other suitable non-cellulosic cationic polymers are disclosed in the CTFA Cosmetic Ingredient Dictionary under the designation "Polyquaternium" followed by a whole number.

Optionally, the inventive compositions may include, in addition, a controlled amount of mono-C$_{14}$–C$_{18}$ alkyl quaternary ammonium salt or di-C$_{12}$–Cl$_{18}$ alkyl (EtO) dimethyl ammonium salt to provide enhanced anti static effect. The mono alkyl quaternary salts have the following formula:

wherein at least three of the R groups are C$_1$–C$_4$ alkyl and at least one is a C$_{10}$–C$_{22}$ alkyl, with X being a salt-forming anion, such as chloride, bromide, methosulfate or ethosulfate. Preferably, the lower alkyl groups will contain one to two carbons, the higher alkyl group will contain 14–18 carbon atoms and the water-solubilizing group will be chlorine or bromine. Suitable compounds include cetyl trimethyl ammonium chloride and stearyl trimethyl ammonium chloride. Alternatively a di (C$_{14}$–C$_{18}$) alkyl (EtO)$_{3-20}$ dimethyl ammonium salt may be employed wherein from 3 to 20 ethoxy groups are present with alkyl substitute. Preferred compounds are di-stearyl (EtO)$_5$ dimethyl ammonium chloride and di-stearyl (EtO)$_{15}$ dimethyl ammonium chloride. If ethoxylated alkyl groups are not present in the di-higher alkyl quaternary salt, the resultant compositions are not clear for example.

Generally the proportion of added mono C$_{14}$–C$_{18}$ alkyl quaternary salt or di C$_{12}$–C$_{18}$ alkyl (EtO)$_{3-20}$ quaternary salt will be from about 0.05% to about 1%, preferably from 0.1% to 0.5%, and most preferably 0.15% to 0.35%, by weight. The anti static effects increase as the proportion of said added quaternary salt increases.

The final essential component in the inventive compositions is water which provides an aqueous medium. Generally, the proportion of water will range from about 51% to about 95%, preferably, about 61% to about 92%, and most preferably about 70% to about 88%, by weight of the resultant composition.

An important characteristic of the inventive compositions is that the sum of the moles of anionic detergent and the moles of anionic hydrotrope is substantially equal to the sum of the moles of amphoteric detergent and the moles of cationic conditioning compound including, optionally, the moles of mono alkyl or dialkylethoxy quaternary anti static compound. On a molar basis the ratio of anionic compounds to amphoteric compounds plus cationic compounds will be the range of about 0.8:1 to about 1.25:1, preferably about 0.9:1 to about 1.10:1, most preferably about 0.95:1 to about 1.05:1. It appears that the proportions of all of the essential ingredients are interrelated and must be controlled in order to achieve compositions having the desired mildness, foaming, cleaning, conditioning, clarity and viscosity characteristics. Generally, the viscosity of the inventive compositions will be in the range of about 1000 to 10,000 cps, preferably 2000 to 7000 cps, and most preferably 3500 cps to 5500 cps, at 24° C., as measured with a Brookfield RVT viscometer using a #4 spindle rotating at 20 rpm.

These inventive compositions are essentially unbuilt liquids, i.e., do not contain detergent building proportions of water-soluble inorganic or organic builder ingredients. Therefore, the resultant compositions are suitable for use as liquid hand washing detergents, liquid shampoos, liquid shower bath products and light duty fabric washing products. Thus, these inventive compositions can contain any of the usual adjuvants found in those compositions provided that they do not interfere with the mildness, performance or clarity characteristics described in the final products. Such additional ingredients include minor proportions of perfumes and coloring ingredients for aesthetic purposes; opacifiers such as ethylene glycol distearate or polystyrene; sequestering agents such as citrate or ethylenediamine tetreaacetate; preservatives such as formaldehyde or Kathon CG® or monomethyloldimethyl hydantoin; fluorescent agents; acids or bases for adjusting pH; and inert salts such as sodium sulfate. The total concentration of added ingredients usually will be less than 5%, preferably less than 3%, by weight of the total composition.

The inventive compositions are prepared by admixing the cationic polymer, if any, with water at a temperature in the range of about 20° C. to 60° C., using sufficient agitation until a clear, homogeneous mixture is formed. Thereafter, the anionic surfactants, namely, the anionic detergent compound and the anionic hydrotropic agent are added while continuing the agitation until a homogeneous mixture is formed. Thereafter, the amphoteric detergent and the silicone ingredient, if any, are added with agitation to the aqueous mixture of cationic polymer and anionic surfactants and agitation is continued until the resultant mixture is homogeneous. Next the disodium phosphate is added to adjust the pH to 6.0–6.5. Next, if the carboxylic acid amine salt is present, a premix of the carboxylic acid and the desired amine is prepared with agitation at a temperature in the range 20° C. to 60° C. Optionally, the perfume is included in this premix which is mixed until homogeneity is achieved. Thereafter, the premix is added to the aqueous detergent mixture with agitation which continues until homogeneity is achieved. Finally the formula amounts of quaternary salt anti-stat, if any, preservative, if any, and color, if any, are added with agitation. During the manufacturing process, mixing is controlled to avoid foaming. The resultant composition is clear and has a pH in the range of about 5.5 to 7.0, preferably from about 6.0 to 6.5.

In the preferred process, the composition is prepared without the addition of external heat. Thus, the process temperature is controlled in the range of 20° C. to 30° C. Using this so-called "cold process" saves energy and the time required to raise or lower the temperature.

Normally, the viscosity and pH of the resultant product is checked before the product is filled into containers for sale. If necessary, additional anionic hydrotrope is added to decrease viscosity or polyethylene glycol (PEG) 18-propylene glycol oleate is added to increase viscosity. Also, if necessary, disodium phosphate dibasic or citric acid or other acid or base is added to adjust the pH. Preferably, the resultant composition is passed through a 20 mesh or equivalent filter prior to filling same into containers for sale.

The foaming properties of the inventive compositions are determined by diluting 15cc of the resultant composition with 85cc of 250 ppm water (40% $Mg^{++}$, 60% $Ca^{++}$), adding 3.0 grams of sebum soil and adjusting the temperature to 25° C. with agitation. Thereafter, the solution is added to a 500 ml graduated cylinder containing a plastic tube filled with water which has a volume of 25cc. The 500 ml glass stoppered cylinder is then rotated through 40 half circles at a speed of 30 rpm. After removing the stopper, the foam volume is read. The cylinder then is removed from the rotation apparatus and placed on a table top. The time interval in seconds is recorded from the completion of rotation until the liquid level in the cylinder reaches 100 ml (75% of the liquid has drained) and the results are recorded as ml of foam/drainage time in seconds. Ml of Foam and drainage times are then expressed on a scale of 1 to 10—1 poorest, 10 best.

The conditioning properties are determined by combing hair tresses treated with the product using the fine teeth of the comb when wet and after drying. In this evaluation 3.2 gm tresses of virgin, European brown hair obtained from DeMeo Brothers, Inc. are prepared with the root end of the hair at the top of the tress. The tresses are rinsed with running tap water at 105° F. (40.5° C.) and then 1 cc of the test product is worked into the tress with the fingers for one minute. The treated tress is rinsed for 30 seconds and a second application of test product is worked into the tress for one minute followed by a 30 second rinsing. Then each tress is rinsed for 60 seconds with 105° F. running tap water and detangled by combing with the wide teeth of the comb. The wetted tresses are maintained wet with deionized water and are combed by expert judges using the fine teeth of the comb. The judges assign a rating of 1 to 10 for each tress, with 10 being easiest to comb. Each tress is combed by a minimum of judges and the ratings are averaged. In the described procedure, the hair tresses are evaluated while wet. The procedure for dry combing is identical except that the hair tresses are dried before being combed.

In the test for evaluation of static, the hair tresses are treated with product as described above and dried. The dried tress is then combed by a skilled evaluator in a forceful, downward manner 20 times using the fine teeth of the comb. The static on each is then evaluated on a scale of 1 to 10 with being excellent. Again, each tress is combed by 10 judges and the ratings are averaged. This evaluation is carried out in a constant temperature—constant humidity room.

Specific inventive liquid compositions are illustrated in the following examples. All quantities indicated in the examples or elsewhere in the specification are by weight unless otherwise indicated. A particularly preferred conditioning shampoo composition according to the described invention is set forth in Example 1 below:

| Example 1 | |
|---|---|
| | by wt. |
| Polyquaternium 10 | 0.60 |
| Sodium lauryl diethenoxy ether sulfate | 7.0 |
| Cocoamidopropyl dimethyl betaine | 7.8 |
| Sodium cumene sulfonate | 1.3 |
| Disodium hydrogen phosphate | 0.3 |
| Dimethylpolyoxyethylene siloxane (DC 5324 fluid) | 0.5 |
| Dimethylpolyoxyethylene/ polyoxypropylene siloxane (DC Q-5220 resin modifier) | 0.5 |
| Laureth-3-carboxylic acid | 0.1 |
| Isostearymidopropyl dimethyl amine | 0.14 |
| PEG 55 - propylene glycol oleate | ±.40 |
| Perfume | 0.5 |
| Kathon CG ® preservative | 0.07 |
| Cetrimonium chloride | 0.25 |

| Example 1 | |
|---|---|
| | by wt. |
| Yellow color solution | 0.14 |
| Water | q.s. |
| | 100.00 |

The foregoing shampoo composition is prepared by the preferred cold process at 20° C.–30° C. without addition of heat. In the cold process, the formula weight of Polyquaternium 10 is admixed with the formula amount of water with agitation to form a clear homogeneous mixture. Thereafter, the alkyl ether sulfate, the sodium cumene sulfonate, the betaine and the two siloxane ingredients are added to the aqueous polyquat solution in sequence with agitation. Mixing is continued after the addition of each ingredient until the resultant mixture is clear and homogeneous, with said agitation being controlled to avoid foaming. Next the disodium phosphate basic is added to said aqueous mixture. Then a homogeneous premix of the formula amounts of laureth-3-carboxylic acid, the isostearylamido-propyl dimethyl amine and perfume is prepared with agitation at a temperature of 20° C.–30° C. and this premix is added to the aqueous detergent mixture with agitation which is continued until the resultant aqueous mixture is clear and homogeneous. Finally, the formula amounts of cetrimonium chloride, preservative and color are added to the foregoing mixture with agitation to form the clear, homogeneous shampoo composition. The resultant shampoo composition has a viscosity of 4500 cps as measured with a Brookfield Viscometer using an RVT spindle #4 rotating at 20 rpm at 25° C. and a pH of 6.25.

When the shampoo composition is tested using the above-described foaming, conditioning and static tests, the following results are obtained:
Foaming—7.0
Conditioning—9.0
Static—9.0

In the composition of Example 1, the molar proportions of the anionic detergent, anionic benzene sulfonate, amphoteric detergent and cationic conditioners follow:

| Sodium lauryl diethenoxy ether sulfate | .01862 |
|---|---|
| Sodium cumene sulfonate | .0058 |
| Cocoamidopropyl dimethyl betaine | .02281 |
| Polyquaternium 10 (monomer m.w. = 504) | .0012 |

Based upon the foregoing analysis, the ratio of the sum of the moles of anionic detergent and benzene sulfonate to the sum of the moles of betaine and cationic conditioner is 0.02493 to 0.02478 or 0.99:1.0.

When the 7% of anionic alkyl diethenoxy ether sulfate is replaced by 5.6% by weight of sodium tetradecyl alkane sulfonates or 5.8% by weight of sodium $C_{14}$–$C_{16}$ alkene sulfonate or 5.3% by weight of ammonium lauryl sulfate— each being equimolar to said ether sulfate—, the resultant compositions have similar characteristics.

EXAMPLES 2–4

The composition of Example 1 is repeated with exceptions that the concentration of Polyquat #10 is reduced to 0.25%, 0.35% and 0.5% by weight respectively and the percentage of PEG—55 propylene glycol oleate is increased to 0.8%, 0.8% and 0.6% by weight respectively, with any balance being water. The resultant clear homogeneous ultramild shampoo compositions yield the foaming, conditioning, static, viscosity and pH results set forth in Table A below:

TABLE A

| Example | 2 | 3 | 4 |
|---|---|---|---|
| Foaming | 7 | 7 | 7 |
| Conditioning | 3 | 5 | 7 |
| Static | 9 | 9 | 9 |
| Viscosity (cps) | 4500 | 4500 | 4500 |
| pH | 6.2 | 6.2 | 6.2 |

EXAMPLES 5–8

The compositions of Examples 1–4 are repeated with the exceptions that 2% by weight of an opacifying agent which is a mixture of ethylene glycol distearate (0.6%) and stearyl alcohol ethoxamer (4) and 0.2% by weight of distearyl dimethyl polyoxyethylene (5) ammonium methyl sulfate are substituted for a like proportion of water. The resultant products are homogeneous, but opaque due to the inclusion of the opacifying agent. Furthermore, the conditioning/static properties are modified due to the inclusion of the added quaternary ammonium salt. The properties of said compositions are shown in Table B below:

TABLE B

| Example | 5 | 6 | 7 | 8 |
|---|---|---|---|---|
| Foaming | 7 | 7 | 7 | 7 |
| Conditioning | 9 | 3 | 5 | 7 |
| Static | 9 | 9 | 9 | 9 |
| Viscosity | 4500 | 4500 | 4500 | 4500 |
| pH | 6.2 | 6.2 | 6.2 | 6.2 |

The addition of the distearethoxy (5) dimethyl ammonium methyl sulfate reduces the molar ratio of anionic compounds to the sum of amphoteric and cationic compounds to 0.98:1.

EXAMPLE 9–12

The conditioning effects of the mixture of laureth-3 carboxylic acid and isostearamidopropyl dimethylamine are set forth in Examples 9–12:

| | % by wt. | | | |
|---|---|---|---|---|
| | 9 | 10 | 11 | 12 |
| Sodium lauryl diethenoxy ether sulfate | 7.0 | 7.0 | 7.0 | 7.0 |
| Cocoamidopropyl dimethyl betaine | 7.8 | 7.8 | 7.8 | 7.8 |
| Sodium cumene sulfonate | 1.3 | 1.3 | 1.3 | 1.3 |
| Disodium hydrogen phosphate | 0.3 | 0.3 | 0.3 | 0.3 |
| Laureth-3 carboxylic acid | 0.1 | 0.3 | 1.0 | 2.0 |
| Isostearamidopropyl dimethyl amine | 0.14 | 0.42 | 1.4 | 2.8 |
| PEG 55 propylene glycol oleate | 0.2 | 0.2 | 0.2 | 0.2 |
| Perfume, color, preservative and water | q.s. | q.s. | q.s. | q.s. |
| | 100.0 | 100.0 | 100.0 | 100.0 |
| Conditioning | 2 | 2.5 | 3 | 3.5 |
| Foaming | 8 | 8.0 | 7 | 6 |
| Clarity | ← clear → | | | |
| Viscosity | 2500 | 3050 | 4100 | 4780 |

These examples illustrate that the amine-acid complexes—amine salts—provide conditioning properties and that the conditioning properties increase as the proportion of the amine-acid complex—amine salt—increases.

However, even at the highest concentration of the amine salt, i.e., 4% by weight because excess amine is present, the conditioning rating is 3.5 which is low. Further, as the level of ethoxylation increases in the carboxylic acid component, the conditioning value decreases because the molar amount of the amine salt produced therefrom decreases.

When stearamidopropyl dimethyl amine is substituted for isostearamidopropyl dimethyl amine in Examples 9–12, the conditioning properties and foaming properties of the final compositions are not changed.

EXAMPLES 13 AND 14

The conditioning effects of cationic cellulosic polyquats in the inventive composition are illustrated in Examples 13 and 14 wherein Polyquaternium 10 is the sole conditioning agent present.

|  | % by wt. | |
|---|---|---|
|  | 13 | 14 |
| Polyquaternium 10 | 0.3 | 0.6 |
| Sodium lauryl diethenoxy ether sulfate | 7.0 | 7.0 |
| Cocoamidopropyl dimethyl betaine | 7.8 | 7.8 |
| Sodium cumene sulfonate | 1.3 | 1.3 |
| Disodium hydrogen phosphate | 0.3 | 0.3 |
| PEG 55 propylene glycol oleate | 0.2 | 0.2 |
| Perfume, color, preservative and water | q.s. | q.s. |
|  | 100.0 | 100.0 |
| Conditioning | 4.0 | 6.75 |
| Foaming | 8.0 | 9.0 |
| Static | 5.0 | 4.0 |
| Clarity | clear | clear |

The foregoing conditioning results show that medium conditioning is obtained when a cationic cellulose polyquat is the sole conditioning agent.

EXAMPLES 15 AND 16

The compositions of Examples 13 and 14 are repeated with the exceptions that 0.24% by weight and 0.48% by weight respectively of Polyquaternium 7 (Merquat 550®) is substituted for the amounts of Polyquaternium 10 and the amine salt produced from 0.1% of laureth-3 carboxylic acid and 0.14% of isostearamidopropyl dimethyl amine is included, with any balance being deducted from the amount of water present. The conditioning, foaming and clarity properties of the resultant compositions are set forth in Table C below:

TABLE C

| Example | 15 | 16 |
|---|---|---|
| Conditioning | 3.5 | 7.0 |
| Foaming | 7.5 | 7.0 |
| Static | 3.0 | 2.0 |
| Clarity | Hazy | Hazy |

Because the compositions are not clear, Polyquaternium 7 as the sole polyquat is not satisfactory.

When Example 16 is repeated using a mixture of 0.3% by weight of Polyquaternium 10 and 0.24% by weight of Polyquaternium 7 in place of 0.48% of Polyquaternium 7, a clear shampoo results having a conditioning rating of 7, a foaming value of 8.5, and a static value of 4.0. This result indicates that a minor proportion—up to about 50% by weight of Polyquaternium 10 may be substituted by Polyquaternium 71—a non cellulosic polyquat—without adversely affecting the clarity of the inventive compositions. Furthermore, the mixture of a cellulosic polyquat with a non-cellulosic polyquat results in a slight increase in conditioning effects.

EXAMPLES 17 AND 18

When the compositions of Examples 15 and 16 are repeated using 0.3% and 0.6% of Polyquaternium 11 (Celquat 200®)—a cellulose polyquat—substituted for 0.24% and 0.48% of Polyquaternium 7, respectively, shampoos having the properties set forth in Table D are obtained.

TABLE D

| Example | 17 | 18 |
|---|---|---|
| Conditioning | 3.0 | 5.0 |
| Foaming | 8.0 | 8.5 |
| Static | 5.0 | 4.5 |

Polyquaternium 11 results in compositions having slightly lower conditioning than Polyquaternium 7.

The compositions of Examples 13–18 above are not within the scope of the claimed invention, but are included herein to further define said invention.

EXAMPLES 19 AND 20

The conditioning properties of polymethylsiloxane in the inventive compositions is illustrated by the following compositions wherein the composition of Example 19 is a control because it contains no conditioning agent.

|  | % by wt. | |
|---|---|---|
|  | 19 | 20 |
| Sodium lauryl diethenoxy ether sulfate | 7.0 | 7.0 |
| Cocoamidopropyl dimethyl betaine | 7.8 | 7.8 |
| Sodium cumene sulfonate | 1.3 | 1.3 |
| Dimethylpolyoxyehtylene siloxane (DC 5324 fluid) | — | 0.5 |
| Dimethylpolyoxyethylene/ polyoxypropyslene siloxane (DC Q-5220 resin modifier) | — | 0.5 |
| Disodium hydrogen phosphate | 0.3 | 0.3 |
| PEG 55 - propylene glycol oleate | 0.2 | 0.2 |
| Perfume, color, preservative, water | q.s. | q.s. |
|  | 100.00 | 100.00 |
| Conditioning | 1.0 | 2.5 |
| Foaming | 7.4 | 7.5 |
| Static | 2.0 | 3.0 |
| Viscosity | 5200 cps | 1100 cps |
| Clarity | clear | clear |

The foregoing compositions demonstrate a conditioning agent must be present in the compositions in order to achieve any conditioning of the hair when shampooed using the inventive composition.

When the composition of Example 20 is repeated with the exception that Silicone DC 5324 is omitted, the resultant composition exhibits a conditioning value of 2.0, a static value of 2.5 and a viscosity of 4000 cps at 25° C. using the Viscometer RVT.

EXAMPLES 21–24

The compositions which follow are preferred compositions containing a mixture of three conditioning agents, each with a different polymethyl siloxane component.

|  | % by wt. | | | |
| --- | --- | --- | --- | --- |
|  | 21 | 22 | 23 | 24 |
| Polyquaternium 10 | 0.6 | 0.6 | 0.6 | 0.6 |
| Sodium lauryl diethenoxy ether sulfate | 7.0 | 7.0 | 7.0 | 7.0 |
| Cocoamidopropyl dimethyl betaine | 7.8 | 7.8 | 7.8 | 7.8 |
| Sodium cumene sulfonate | 1.7 | 1.3 | 1.3 | 1.3 |
| Disodium hydrogen phosphate | 0.3 | 0.3 | 0.3 | 0.3 |
| Laureth-3-carboxylic acid | 0.1 | 0.1 | 0.1 | 0.1 |
| Isostearymidopropyl dimethyl amine | 0.14 | 0.14 | 0.14 | 0.14 |
| Trimethylsilylamodimethicone (DC Q2-8220) | 0.5 | — | — | — |
| Silicone quaternium 2 (Silquat 100) | — | 0.5 | — | — |
| Silicone quaternium 2 (Silquat 300) | — | — | 0.5 | — |
| Dimethicone copolyol amine (Silamine 50) | — | — | — | 0.5 |
| PEG 55 - propylene glycol oleate |  |  |  |  |
| Perfume, color, preservative, water | q.s. | q.s. | q.s. | q.s. |
|  | 100.00 | 100.00 | 100.00 | 100.00 |
| Conditioning | 8.0 | 8.0 | 8.0 | 8.0 |
| Foaming | 8.0 | 7.0 | 7.0 | 7.0 |
| Static | 4.0 | 4.0 | 4.0 | 4.0 |
| Clarity | clear | clear | clear | clear |
| Viscosity (cps) | 1000 | 4000 | 4000 | 4000 |

EXAMPLES 25 AND 26

When the composition of Example 21 is repeated with the exceptions that the amount of sodium cumene sulfonate is reduced to 1.3% by weight and 0.1% and 0.25%, respectively, of centrimonium chloride is added, with any difference being water, shampoo compositions having the properties shown in Table E are obtained.

TABLE E

| Example | 25 | 26 |
| --- | --- | --- |
| Conditioning | 8.0 | 8.0 |
| Foaming | 8.0 | 7.0 |
| Static | 6.0 | 7.0 |
| Clarity | clear | clear |
| Viscosity (cps) | 1000 | 1500 |

EXAMPLES 27 AND 28

These examples show other compositions which are within the scope of the described invention and their properties.

|  | % by wt. | |
| --- | --- | --- |
|  | 27 | 28 |
| Polyquaternium 10 | 0.9 | 0.3 |
| Sodium lauryl diethenoxy ether sulfate | 10.5 | 3.5 |
| Cocoamidopropyl dimethyl betaine | 11.7 | 3.9 |
| Sodium cumene sulfonate | 1.95 | 0.65 |
| Disodium hydrogen phosphate | 0.45 | 0.15 |
| Laureth-3 carboxylic acid | 0.15 | 0.05 |
| Isostearymidopropyl dimethyl amine | 0.21 | 0.07 |
| Silicone DC 5220 | 0.75 | 0.25 |
| Silicone DC 5324 | 0.75 | 0.25 |
| PEG 55 - propylene glycol oleate | 0.6 | 0.2 |
| Cetyltrimethyl ammonium chloride | 0.375 | 0.125 |
| Water | q.s. | q.s. |
|  | 100.00 | 100.00 |
| Conditioning | 9.0 | 6.0 |
| Foaming | 8.0 | 4.0 |
| Static | 9.0 | 9.0 |
| Clarity | clear | clear |

-continued

|  | % by wt. | |
| --- | --- | --- |
|  | 27 | 28 |
| Viscosity | 10000 | 1900 |
| pH | 6.2 | 6.35 |

Example 28 illustrates that foaming is reduced when a proportion of 8% by weight of the detersive surfactant is employed. Further, as expected, good foaming is achieved when the proportion of detersive surfactant is increased to 24.2% by weight of the composition.

EXAMPLES 29 AND 30

The following compositions illustrate the importance of the presence of the anionic hydrotropic sulfonate/sulfate in the described compositions.

|  | % by wt. | |
| --- | --- | --- |
|  | 29 | 30 |
| Sodium lauryl diethenoxy ether sulfate | 7.0 | 9.2 |
| Cocoamidopropyl dimethyl betaine | 7.8 | 7.8 |
| Disodium hydrogen phosphate | 0.3 | 0.3 |
| Water | q.s. | q.s |
|  | 100.00 | 100.00 |
| Conditioning | 1.0 | 1.0 |
| Foaming | 4.5 | 4.0 |
| Static Control | 2.0 | 2.0 |
| Clarity | clear | clear |
| Viscosity | 10050 | 10100 |

Example 30 differs from Example 29 in that the molecular proportion of anionic detergent is increased to be equivalent to the sum of the molar proportion of anionic detergent and anionic hydrotropic sulfonate shown in the control formulation of Example 19.

Comparison of Examples 27 and 28 compositions with the Example 19 composition illustrates that omission of the anionic hydrotrope ingredient from the inventive compositions results in a significant reduction in foaming and a doubling in viscosity. In these examples, the applicable molar ratios of anionic compounds to amphoteric plus cationic compounds are 0.78:1 and 1.03:1 respectively. Thus, the presence of the anionic hydrotrope sulfonate/ sulfate ingredient is essential in the claimed detersive surfactant mixture of the inventive compositions.

When like molar proportions of cocyl isothionate anionic detergent, hydrotropic sodium xylene sulfonate, hydrotropic hexyl sulfate, lauryl trimethyl betaine, sodium cocoyl amphoprionate and laurylamidoethyl sultaine are substituted for the corresponding components in the above examples, compositions having similar performance and physical characteristics are obtained. The resultant products are effective for conditioning hair and skin and, therefore, are useful for cleansing the hair and skin.

Although the need for substantially balanced molar proportions of anionic materials—detergent plus hydrotropic sulfonate/sulfate—and amphoteric plus cationic ingredients is not understood, it is believed that the anionic ingredients and the amphoteric plus cationic materials form a complex—possibly two complexes. The existence of at least one complex is suggested by the improved mildness and the increased viscosity of the resultant mixtures. It is further suggested by the improved conditioning properties when conditioning agents are included. While the actual mechanism is not understood, the efficacy of the resultant compositions is apparent at use concentrations thereof.

The clear ultra mild compositions of the present invention can also be formulated as anti-dandruff shampoos, by employing therein about 0.10% to about 4% by weight of a conventional anti-dandruff therapeutic agent which is soluble in the detersive surfactant mixture. Such agents include: 1-imidazolyl-1-(4-chlorophenoxy)-3,3-dimethylbutan-2-one (Climbazole); acetylsalicylic acid; salicylic acid; 2,4,4,'-trichloro-2'-hydroxy diphenyl ether (triclosan); 1-acetyl-4-(4-((2-(2,4dichlorophenyl)-2-(1H-imidazolyl-1-methyl)-1,3-dioxolan-4-yl)methoxy)phenyl)-piperazine (ketoconazole); 1-hydroxy-4-methyl-6-(2,4,4-trimethylpentyl)-2-pyridone monoethonolamine salt (picrotone olamine); and mixtures thereof. Climbazole is the preferred anti-dandruff therapeutic agent.

EXAMPLES 31 AND 32

These examples illustrate clear antidandruff compositions which are within the scope of the described invention.

|  | % by wt. | |
| --- | --- | --- |
|  | 31 | 32 |
| Polyquaternium 10 | 0.6 | 0.6 |
| Sodium lauryl diethenoxy ether sulfate | 7.0 | 7.0 |
| Cocoamidopropyl dimethyl betaine | 7.8 | 7.8 |
| Sodium cumene sulfonate | 1.3 | 2.17 |
| Disodium hydrogen phosphate | 0.1 | 0.3 |
| Laureth - 3 carboxylic acid | 0.1 | 0.1 |
| Isostearymidopropyl dimethyl amine | 0.14 | 0.14 |
| Silicone DC 5220 | 0.24 | — |
| Silicone DC 5324 | 0.44 | — |
| Silicone DC Q2-8220 | — | 0.5 |
| PEG 55 - propylene glycol oleate | 0.36 | — |
| PEG 18 - glyceryl glycol dioleococoate | — | 0.2 |
| Cetyltrimethyl ammonium chloride | 0.25 | 0.25 |
| Climbazole | 0.5 | 0.5 |
| Color, perfume, preservative, water | q.s. | q.s. |
|  | 100.00 | 100.00 |

The invention has been described with respect to various examples and illustrations thereof but is not to be limited to these because it is clear that one of skill in the art, with the present description before him, will be able to utilize substitutes and equivalents without departing from the invention.

What is claimed is:

1. A clear, ultra mild, aqueous, foaming and conditioning detergent composition comprising by weight,
  A. about 5% to about 40% of a detersive surfactant mixture of:
    (1) about 2% to about 14% of an anionic detergent selected from the group consisting of $C_8$–$C_{18}$ alkyl sulfates, $C_8$–$C_{18}$ alkyl ethenoxy ether sulfate containing 1 to 5 ethenoxy groups in the molecule, $C_8$–$C_{18}$ acyl isethionates, $C_{10}$–$C_{20}$ allyl sulfonates, $C_{10}$–$C_{22}$ alkene sulfonates, and mixtures thereof;
    (2) about 0.5% to about 5% of an anionic hydrotropic, $C_1$–$C_3$ alkyl benzene sulfonate or $C_5$–$C_6$ alkyl sulfate; and
    (3) about 2.5% to about 21% of an amphoteric surfactant selected from the group consisting of $C_8$–$C_{18}$ alkyl betaines, and sulfobetaines, $C_8$–$C_{18}$ alkyl amido, $C_2$–$C_3$ alky betaines and sulfobetaines, $C_8$–$C_{18}$ alkyl amphoacetates, $C_8$–$C_{18}$ alkyl amphopropionates, and mixtures thereof;
  B. about 0.05% to about 9% by weight of a water-insoluble conditioning agent which is soluble in said detersive surfactant mixture and which comprises 0.05% to 5% of a complex of essentially equimolar amounts of a $C_8$–$C_{18}$ (EtO)$_{1-10}$ carboxylic acid, and a $C_8$–$C_{18}$ alkyl (EtO)$_{0-10}$ dimethyl amine and at least one member selected from the group consisting of:
    (1) 0.25% to 3% of a water-insoluble silicone which is soluble in said aqueous detersive surfactant mixture and is selected from the group consisting of polydimethylsiloxane polyether copolymers, polydimethylsiloxanes containing an amino substituent, polydimethylsiloxanes containing at least one ammonia substituent and mixtures thereof;
    (2) a mixture of the water-insoluble conditioning agent with about 0.1 to 1.0% of a polyquaternary compound selected from the group consisting of a quaternized cellulosic polymer and a mixture of the quaternized cellulosic polymer with a non-cellulosic quaternary conditioning polymer; and
    (3) a mixture of the water-insoluble conditioning agent and B(1) with about 0.1 to 1.0% of a polyquaternary compound selected from the group consisting of a quaternized cellulosic polymer and a mixture the quaternized cellulosic polymer with a non-cellulosic quaternary conditioning polymery; and
  C. the balance of an aqueous medium; the sum of the moles of anionic detergent and anionic benzene sulfonate being substantially equal to the sum of the moles of amphoteric detergent and catonic conditioning agent at a pH in the range of 5.5 to 7.0 and said composition being effective to deliver said conditioning agent in water insoluble form at use concentrations of the composition in water.

2. A detergent composition according to claim 1 wherein the mole ratio of the sum of the moles of anionic detergent and the moles of anionic hydrotrope to the sum of the moles of amphoteric detergent and the moles of cationic conditioning agent is in the range of about 0.8:1 to 1.25:1.

3. A detergent composition according to claim 2 wherein said conditioning agent is said complex of said ethoxylated carboxylic acid and said alkyl amine, said detergent composition providing a low level of conditioning at use concentrations.

4. A detergent composition according to claim 2 wherein said conditioning agent is said water-insoluble silicone which is soluble in the aqueous detersive surfactant mixture, said detergent composition providing a low level of conditioning at use concentrations.

5. A detergent composition according to claim 3 wherein said conditioning agent further includes a quaternized cellulosic polymer, said detergent composition providing a high level of conditioning at use concentrations.

6. A detergent composition according to claim 4 wherein said conditioning agent further includes a quaternized cellulosic polymer, said detergent composition providing a high level of conditioning at use concentrations.

7. A detergent composition according to claim 2 wherein said conditioning agent is a mixture of said complex of carboxylic acid and amine and said water-insoluble silicone and a quaternized cellulose polymer, said detergent composition providing a high level of conditioning at use concentrations.

8. A detergent composition according to claim 2 which includes, in addition, from about 0.05% to about 1.0% by weight of either a mono-$C_{10}$-$C_{22}$ alkyl tri $C_1$-$C_4$ alkyl ammonium salt or a di($C_{14}$-$C_{18}$ alkyl) (EtO)$_{3-20}$ di-$C_1C_4$ alkyl ammonium salt as an anti static agent.

9. A detergent composition according to claim 2 which includes, in addition, from about 0.1% to about 4% by weight of an anti-dandruff therapeutic agent, which agent is soluble in the detersive surfactant mixture.

10. A detergent composition according to claim 9 wherein said anti-dandruff therapeutic agent is selected from the group consisting of: 1-imidazolyl-1-(4-chlorophenoxy)-3,3-dimethylbutan-2-one (climbazole); acetylsalicylic acid; salicylic acid; 2,4,4,'-trichloro-20'-hydroxy diphenyl ether (triclosan); 1-acetyl-4-(4-( (2-(2,4-dichlorophenyl)-2-(1H-imidazolyl-1-methyl)-1,3-dioxolan-4-yl)methoxy)phenyl)-piperazine (ketoconazole); 1-hydroxy-4-methyl-6-(2,4,4-trimethylpentyl)-2-pyridone monoethonolamine salt (picrotone olamine); and mixtures thereof.

11. The detergent composition according to claim 10 wherein said anti-dandruff therapeutic agent is 1-imidazolyl-1-(4-chlorophenoxy)-3,3-dimethylbutan-2-one (climbazole).

12. A clear detergent composition according to claims 2 or 9 which further includes an opacifying or pearlizing agent to render the composition opaque or pearlized.

13. The detergent composition according to claim 12 wherein said opacifying or pearlizing agent is selected from the group consisting of ethylene glycol distearate, polystyrene and mixtures thereof.

14. A clear, ultra-mild, foaming and conditioning detergent composition comprising, by weight:
   A. about 8% to about 28% of a detersive surfactant mixture of:
      (1) about 4% to about 11% of an anionic detergent selected from the group consisting of $C_8$-$C_{18}$ alkyl sulfates and $C_8$-$C_{18}$ alkyl (ethenoxy) 1–5 ether sulfates;
      (2) about 1% to about 4% of a water soluble salt of an anionic hydrotropic, $C_1$-$C_3$ alkyl benzene sulfonate; and
      (3) about 4% to about 13% of an amphoteric surfactant selected from the group consisting of $C_8$-$C_{18}$ alkyl betaines and $C_8$-$C_{18}$ alkylamido, $C_2$-$C_3$ alkyl betaines;
   B. about 0.05% to 9.0% by weight of a water-insoluble conditioning agent which is soluble in said detersive surfactant mixture and which comprises about 0.1% to about 2.5% of a complex of essentially equimolar amounts of a $C_8$-$C_{18}$ (EtO) carboxylic acid, and a $C_8$-$C_{18}$ alkyl (EtO)$_{0-10}$ dimethyl amine and at least one member selected from the group consisting of:
      (1) about 0.5% to about 2% of a water-insoluble silicone which is soluble in said aqueous detersive surfactant mixture and is selected from the group consisting of polydimethyl siloxane polyether copolymers, polydimethylsiloxanes containing an amino substituent, polydimethylsiloxanes containing at least one ammonia substituent and mixtures thereof;
      (2) a mixture of the water-insoluble conditioning agent with about 0.1 to about 0.8% of a polyquaternary compound selected from the group consisting of a quaternized cellulosic polymer and a mixture of the quaternized cellulosic polymer with a non-cellulosic quaternary conditioning polymer; and
      (3) a mixture of the water-insoluble conditioning agent and B(1) with about 0.1 to about 0.8% of a polyquaternary compound selected from the group consisting of a quaternized cellulosic polymer and a mixture of the quaternized cellulosic polymer with a non-cellulosic quaternary conditioning polymer; and
   C. about 61% to about 92% of water; the molar ratio of the sum of the moles of anionic detergent and anionic benzene sulfonate to the sum of the moles of amphoteric detergent and cationic conditioning agent at a pH in the range of about 6 to 6.5 being from about 0.9:1 to about 1:1, said composition being effective to deliver said conditioning agent in water-insoluble form at use concentrations of the composition in water.

15. A detergent composition according to claim 14 wherein said conditioning agent is said complex of said ethoxylated carboxylic acid and said alkyl amine, said detergent composition providing a low level of conditioning at use concentrations.

16. A detergent composition according to claim 14 wherein said conditioning agent is said water-insoluble silicone which is soluble in the aqueous detersive surfactant mixture, said detergent composition providing a low level of conditioning at use concentrations.

17. A detergent composition according to claim 15 wherein said conditioning agent further includes a quaternized cellulosic polymer, said detergent composition providing a high level of conditioning at use concentrations.

18. A detergent composition according to claim 16 wherein said conditioning agent further includes a quaternized cellulosic polymer, said detergent opposition providing a high level of conditioning at use concentrations.

19. A detergent composition according to claim 14 wherein said conditioning agent is a mixture of said complex of carboxylic acid and amine, and said water-insoluble silicone and a quaternized cellulose polymer, said detergent composition providing a high level of conditioning at use concentrations.

20. A detergent composition according to claim 14 which includes, in addition, from about 0.05% to about 1.0% by weight of either a mono-$C_{10}$-$C_{22}$ alkyl tri $C_1$-$C_4$ alkyl ammonium salt or a di($C_{14}$-$C_{18}$ alkyl) (EtO)$_{3-20}$ di-$C_1$-$C_4$ alkyl ammonium salt as an anti static agent.

21. A detergent composition according to claim 14 which includes, in addition, from about 0.1% to about 4% by weight of an anti-dandruff therapeutic agent, which agent is soluble in the detersive surfactant mixture.

22. A detergent composition according to claim 14 wherein said anti-dandruff therapeutic agent is selected from the group consisting of: 1-imidazolyl-1-(4-chlorophenoxy)-3,3-dimethylbutan-2-one (climbazole); acetylsalicylic acid; salicylic acid; 2,4,4,'-trichloro-2'-hydroxy diphenyl ether (triclosan); 1-acetyl-4-(4-( (2-(2,4-dichlorophenyl)-2-(1H-imidazolyl-1-methyl)1,3-dioxolan-4-yl)methoxy)phenyl)-piperazine (ketoconazole); 1-hydroxy-4-methyl-6-(2,4,4-trimethylpentyl)-2-pyridone monoethonolamine salt (picrotone olamine); and mixtures thereof.

23. The detergent composition according to claim 22 wherein said anti-dandruff therapeutic agent is 1-imidazolyl-1-(4-chlorophenoxy)-3,3-dimethylbutan-2-one (climbazole).

24. A clear detergent composition according to claims 14 or 21 which further includes an opacifying or pearlizing agent to render the composition opaque or pearlized.

25. The detergent composition according to claim 24 wherein said opacifying or pearlizing agent is selected from the group consisting of ethylene glycol distearate, polystyrene and mixtures thereof.

26. A clear, ultra-mild, foaming and conditioning detergent composition comprising, by weight:
   A. about 13% to about 22% of a detersive surfactant mixture of:
      (1) about 6% to about 8% of an anionic detergent selected from the group consisting of $C_8$–$C_{18}$ alkyl sulfates and $C_8$–$C_{18}$ alkyl (ethenoxy) 1–5 ether sulfates;
      (2) about 1% to about 4% of a water soluble salt of an anionic hydrotropic, $C_1$–$C_3$ alkyl benzene sulfonate; and
      (3) about 6% to about 10% of an amphoteric surfactant selected from the group consisting of $C_8$–$C_{18}$ alkyl betaines and $C_8$–$C_{18}$ alkylamido, $C_2$–$C_3$ alkyl betaines;
   B. about 0.05% to 9.0% by weight of a water-insoluble conditioning agent which is soluble in said detersive surfactant mixture and which comprises about 0.15% to about 1.5% of a complex of essentially equimolar amounts of a $C_8$–$C_{18}$ (EtO)$_{2-10}$ carboxylic acid, and a $C_8$–$C_{18}$ alkyl (EtO)$_{0-10}$ dimethyl amine and at least one member selected from the group consisting of:
      (1) about 0.7% to about 1.5% of a water-insoluble silicone which is soluble in said aqueous detersive surfactant mixture and is selected from the group consisting of polydimethyl siloxanepolyether copolymers, polydimethylsiloxanes containing an amino substituent, polydimethylsiloxanes containing at least one ammonia substituent and mixtures thereof;
      (2) a mixture of the water-insoluble conditioning agent with about 0.2 to about 0.7% of a polyquaternary compound selected from the group consisting of a quaternized cellulosic polymer and a mixture of the quaternized cellulosic polymer with a non-cellulosic quaternary conditioning polymer; and
      (3) a mixture of the water-insoluble conditioning agent and B(1) with about 0.2 to 0.7% of a polyquaternary compound selected from the group consisting of a quaternized cellulosic polymer and a mixture of the quaternized cellulosic polymer with a non-cellulosic quaternary conditioning polymer; and
   C. about 70% to about 88% of water; the molar ratio of the sum of the moles of anionic detergent and anionic benzene sulfonate to the sum of the moles of amphoteric detergent and cationic conditioning agent at a pH in the range of about 6 to 6.5 being from about 0.95:1 to about 1.05:1, said composition being effective to deliver said conditioning agent in water-insoluble form at use concentrations of the composition in water.

27. A detergent composition according to claim 26 wherein said conditioning agent is a mixture of said complex of carboxylic acid and amine and said water-insoluble silicone and a quaternized cellulose polymer, said detergent composition providing a high level of conditioning at use concentrations.

28. A detergent composition according to claim 26 which includes, in addition, from about 0.05% to about 1.0% by weight of either a mono-$C_{10}$–$C_{22}$ alkyl tri $C_1$–$C_4$ alkyl ammonium salt or a di($C_{14}$–$C_{18}$ alkyl) (EtO)$_{3-20}$ di-$C_1$–$C_4$ alkyl ammonium salt as an anti static agent.

29. A detergent composition according to claim 28 which includes, in addition, from about 0.1% to about 4% by weight of an anti-dandruff therapeutic agent, which agent is soluble in the detersive surfactant mixture.

30. A detergent composition according to claim 29 wherein said anti-dandruff therapeutic agent is selected from the group consisting of: 1-imidazolyl-1-(4-chlorophenoxy)-3,3-dimethylbutan-2-one (climbazole); acetylsalicylic acid; salicylic acid; 2,4,4,'-trichloro-2'-hydroxy diphenyl ether (triclosan); 1-acetyl-4-(4-( (2-(2,4-dichlorophenyl)-2-(1H-imidazolyl-1-methyl)-1,3-dioxolan-4-yl)methoxy)phenyl)-piperazine (ketoconazole); 1-hydroxy-4-methyl-6-(2,4,4-trimethylpentyl)-2-pyridone monoethonolamine salt (picrotone olamine); and mixtures thereof.

31. The detergent composition according to claim 30 wherein said anti-dandruff therapeutic agent is 1-imidazolyl-1-(4-chlorophenoxy)-3,3-dimethylbutan-2-one (climbazole).

32. A clear detergent composition according to claims 26 or 29 which further includes an opacifying or pearlizing agent to render the composition opaque or pearlized.

33. The detergent composition according to claim 32 wherein said opacifying or pearlizing agent is selected from the group consisting of ethylene glycol distearate, polystyrene and mixtures thereof.

* * * * *